United States Patent [19]

Tosswill

[11] 4,090,080
[45] May 16, 1978

[54] IMAGING

[75] Inventor: Christopher H. Tosswill, Sturbridge, Mass.

[73] Assignee: Galileo Electro-Optics Corp., Sturbridge, Mass.

[21] Appl. No.: 646,917

[22] Filed: Jan. 6, 1976

[51] Int. Cl.² ............................................. G01T 1/20
[52] U.S. Cl. .................................. 250/366; 250/505; 250/578
[58] Field of Search ................. 250/578, 505, 394, 366

[56] References Cited

U.S. PATENT DOCUMENTS

| | | | |
|---|---|---|---|
| 3,291,988 | 12/1966 | Chope et al. | 250/366 |
| 3,291,990 | 12/1966 | Lentz | 250/366 |
| 3,684,886 | 6/1972 | Muehllegner | 250/366 |
| 3,746,454 | 7/1973 | Pace et al. | 250/578 |

Primary Examiner—Harold A. Dixon
Assistant Examiner—T. N. Grigsby

[57] ABSTRACT

Obtaining information about positional source of, for example, a gamma ray source, by slit collimating and detecting beam components from the source in a multiplicity of varying slit locations, and using the resulting data to plot the source position.

29 Claims, 10 Drawing Figures

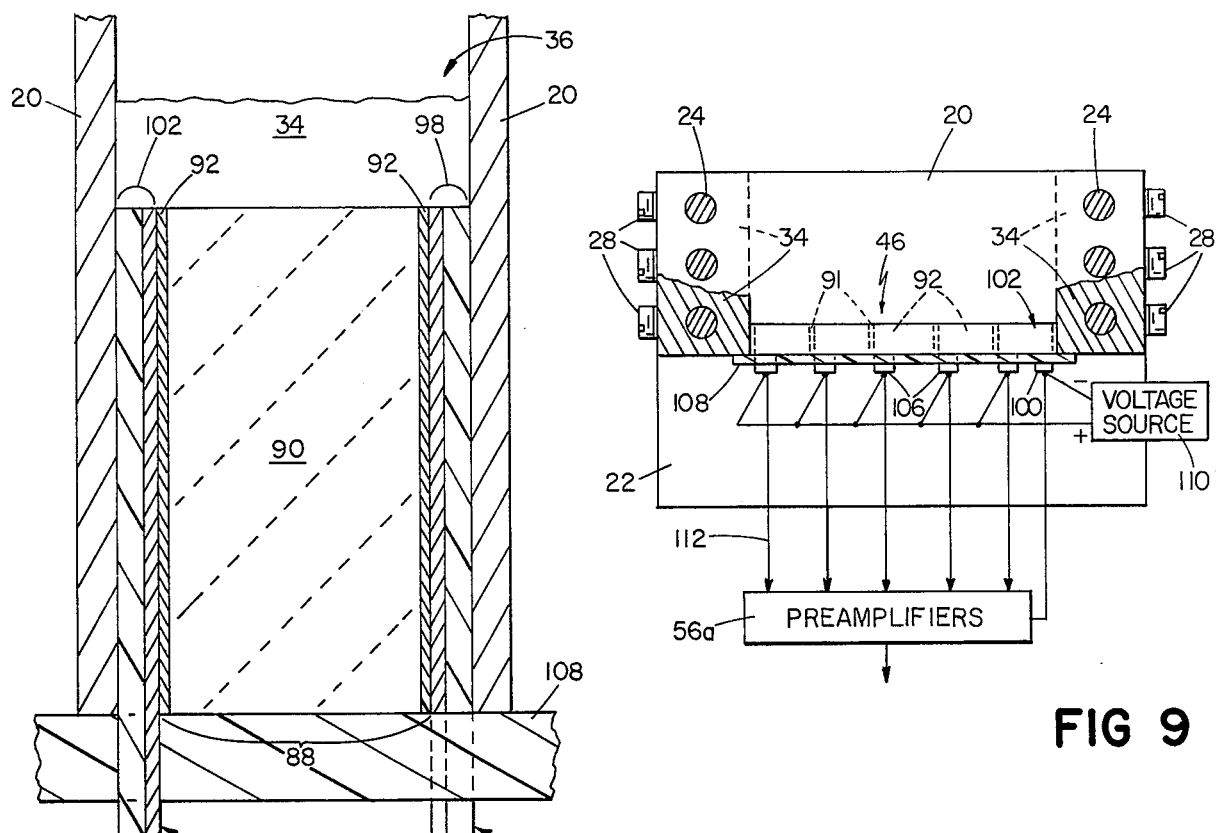
FIG 8
FIG 9
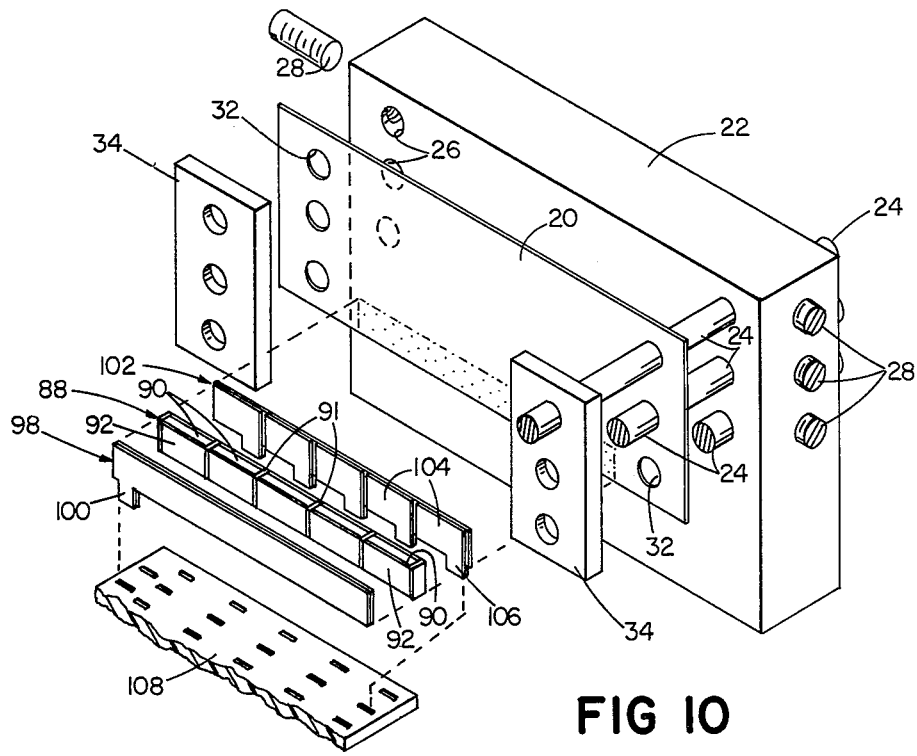
FIG 10

IMAGING

BACKGROUND OF THE INVENTION

This invention relates to devices for obtaining information about radiation sources.

Visible light can be both reflected and refracted. The ordinary camera takes advantage of refraction by using an optical lens to refract and focus the visible light coming from an object, in order to produce an image of the object on film. However, electromagnetic radiation of higher frequency than vacuum ultraviolet (such as X rays and gamma rays, together referred to hereinafter as "gamma radiation") cannot be efficiently either reflected or refracted. Therefore the formation of an image of a source of gamma radiation has been achieved with the use of a collimator, which operates in somewhat similar fashion to the old pinhole camera. The pinhole camera permits the light from an object to pass in a straight line through a pinhole in the camera box, to produce an inverted image on the film.

Collimators with an array of parallel channels, such as the one depicted in FIG. 1, have been used in the imaging of gamma radiation sources. With the axes of the channels pointed toward a gamma radiation source, the channels are generally the same size in both dimensions normal to the axis; usually the channels are circular, triangular, or square in cross section. In FIG. 1, with the walls or septa of each channel made of lead to absorb gamma radiation, and with a radiation detector (not shown) placed on the side of the collimator opposite the source, the radiation that can pass from a point source through a particular channel and reach the detector is defined by the solid angle (A) subtended by the base of the collimating channel 2. Spatial resolution of such a collimator is improved by reducing the solid angle. However, the sensitivity of each channel, which increases as does the amount of radiation passing through the channel, is improved by increasing the solid angle. Of course it is desirable to improve both spatial resolution and sensitivity, the latter particularly so that the necessary time of observation may be reduced.

Turning to the radiation detector, it is known to use the photoconductor as the basic element of such a detector. However, in known arrays of photoconductor detector elements the photon absorption distance and the interelectrode distance correspond to the same photoconductor dimension, and thus are generally the same length. It would be desirable to make the photon absorption distance large with respect to the interelectrode distance, for the larger the absorption distance, the better the sensitivity, because a larger fraction of the incident photons are collected, and the smaller the interelectrode distance, the greater the efficiency, and also the rapidity, of collection at the electrodes of electrical signals created in the photoconductor body by incident photons.

SUMMARY OF THE INVENTION

The invention provides a sensitive, fast, high resolution, and convenient-to-use device for obtaining information about the distribution of a gamma radiation source, and further provides a radiation detector useful in such a device.

The information-obtaining device of the invention has high sensitivity without sacrifice of resolution. The device includes a collimator that is easy to construct, without the necessity for an intricate honeycomb of separate channels, and the septa of the collimator can be conveniently made of tungsten foil, tungsten being a better radiation-absorbing material than lead, and thus can be thinner than lead septa, thereby improving the effective collimator transparency. The output of the device can be readily and rapidly transformed by conventional computer techniques to provide highly resolved images of gamma radiation sources. The device has substantial present application in the field of nuclear medicine, and also has industrial application.

The detector of the invention is easy to construct, and has an improved resolution and signal-to-noise ratio. It has a high uniformity of response to a given incident photon energy so that noise and spurious signals caused by Compton effect scattered, lower energy photons originating at sites remote from the primary radiation sources can be rejected. It also has a high photon collection efficiency, for improved sensitivity, and a brief output pulse, for improved temporal resolution.

The invention features in one aspect obtaining information about positional source of, for example, a gamma ray source, by slit collimating and detecting beam components from the source in a multiplicity of varying slit locations, and using the resulting data to plot the source position.

Preferred embodiments of the invention feature in this aspect a collimator including a frame having an axis of rotation and a plurality of flat sheets of gamma-radiation-absorbing material maintained by the frame in parallel, spaced-apart relation with respect to each other and parallel with the axis of rotation, adjacent pairs of the sheets defining slits therebetween, each of the slits having an opening at one end thereof and a base at the opposite end thereof and being unimpeded, for permitting passage of gamma radiation therethrough, in a first direction parallel to the axis of rotation, and being unimpeded, within the frame, in a second direction perpendicular to the axis of rotation and parallel with the sheets, means for positioning the collimator to maintain the axis of rotation pointed at a gamma radiation source so that the slits are disposed to receive gamma radiation therefrom while the collimator is rotated about the axis, each of the slits subtending, in the plane defined by the first and second directions, a much larger angle for receiving radiation passing therethrough to the base thereof from the source than it subtends in a second plane perpendicular to the second direction, a detector effectively connected to the frame for common rotation with the collimator and positioned adjacent the bases of the slits for detecting radiation passing through each slit to the base thereof and providing an output representative of intensity of detected radiation over the whole base of each slit as a function of the angle of rotation of the collimator, and means for accumulating a matrix of such outputs, the matrix being ordered according to the particular slit in which the radiation causing the output was detected and according to the particular angle of rotation of said collimator at the time the radiation was detected, the matrix being suitable for transformation to a matrix corresponding to the image of the source.

The invention features in another aspect a detector for detecting gamma radiation and for providing an output in response to the radiation, the detector comprising a plurality of detector elements of photoconductor material sensitive to gamma radiation, the elements being strips arranged in parallel, spaced-apart relation, to expose to incident gamma radiation from a source of the same a generally planar surface made up of one face from each of the elements, each of the elements having a pair of electrodes affixed thereto, each one of the pair of electrodes being positioned between adjacent elements, the planes of electrodes being perpendicular to the planar surface exposed to incident radiation, and the thickness of each detector element measured from the surface exposed to incident radiation along a perpendicular line therefrom is large with respect to the distance between each pair of electrodes.

Certain preferred embodiments feature a detector comprising a plurality of detector elements equal in number to the slits, the elements being effectively connected to the frame so that they remain positioned adjacent their respective bases while the collimator is rotated about the axis; processing circuitry including an amplifier for amplifying detector outputs and an amplitude discriminator for discarding from the outputs any components having below a minimum amplitude; a housing as the maintaining means, the housing including a tube, a plate rotatably mounted in the tube, and means for rotating the plate, the plate containing an aperture for receiving the frame so that when the plate is rotated, the frame is rotated together therewith; an indexed motor adapted to rotate the plate in discrete angular steps as the rotating means; collimator sheets made of tungsten foil; a detector element including a scintillating sheet and a photomultiplier connected to the sheet for providing an electrical output; optical fibers interconnecting the scintillating sheet with its photomultiplier; and detector elements positioned between the collimator sheets at the base of the slits and maintained there by the frame. Other preferred embodiments feature detector elements of photoconductor material; detector elements composed of cadmium telluride; photoconductor detector elements the planes of whose electrodes are parallel to the collimator sheets and the distance through the photoconductor element in the first direction is large with respect to the distance between each pair of electrodes in a third direction perpendicular to the first and second directions; a distance through the photoconductor element in the first direction no less than 5 mm and the distance through the photoconductor element in the third direction no greater than 0.75 mm; and photoconductor elements in the form of strips.

Other advantages and features of the invention will be apparent from the description and drawings herein of preferred embodiments thereof.

BRIEF DESCRIPTION OF THE DRAWINGS

FIG. 8 is a greatly enlarged sectional view, along a vertical plane, of a portion of a second embodiment of the invention;

FIG. 9 is a sectional view, along a vertical plane perpendicular to the plane of FIG. 8, of said second embodiment, with portions broken away and with associated circuitry shown diagrammatically; and FIG. 10 is an exploded isometric view of a portion of said second embodiment.

DESCRIPTION OF THE PREFERRED EMBODIMENTS

Figure 1:
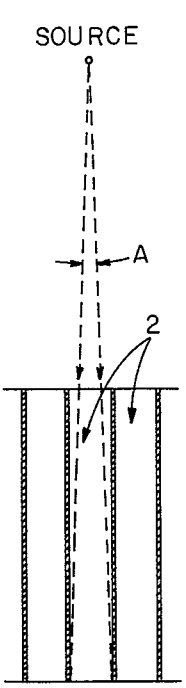
FIG. 1 is a sectional view, along a vertical plane, of a typical known channel collimator.
Figure 2:
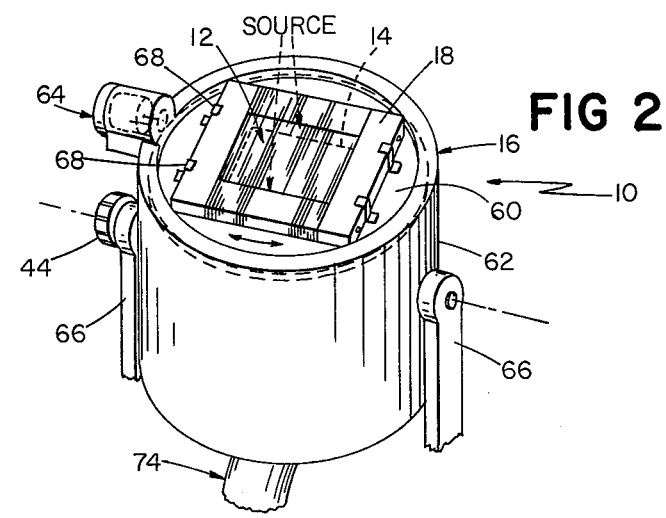
FIG. 2 is a view in perspective of one embodiment of the invention.
Figure 3:
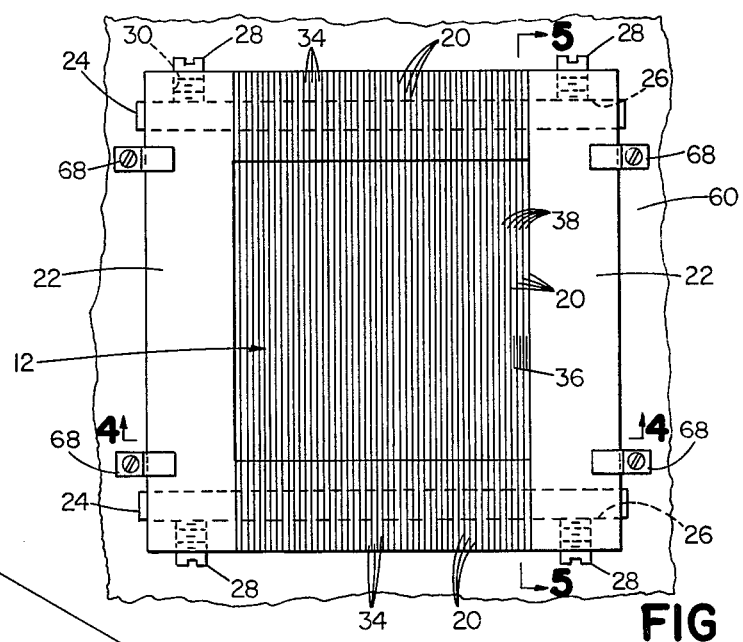
FIG. 3 is an enlarged plan view of a portion of the embodiment of FIG. 2.
Figure 6:
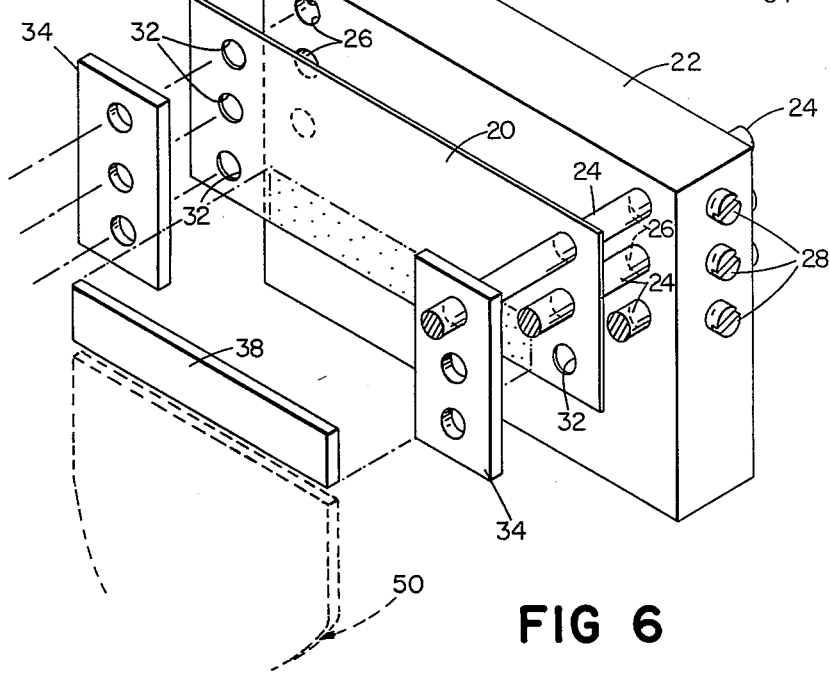
FIG. 6 is an exploded isometric view of a portion of the embodiment of FIG. 3.

Camera 10, which embodies the invention, is shown in FIG. 2, and comprises an integrated collimator 12 and detector 14 mounted for rotation together in housing 16. Collimator 12, as better shown in FIGS. 3 through 6, includes frame 18 made of steel and a series of fifty-one parallel sheets 20 of tungsten foil held in tension in frame 18. Frame 18 has two opposte sides 22, which are 80 mm by 55 mm by 15 mm. A set of three steel 5 mm diameter rods 24 connects sides 22 at the ends thereof through holes 26 drilled through sides 22. Screws 28 when tightened in holes 20, which intersect holes 26 transversely, hold rods 24 in place in sides 22, and form a square having an outer dimension of about 80 mm by 80 mm. Sheets 20 also have a set of three holes 32 (FIG. 6) at their ends, to receive rods 24, which thereby maintain sheets 20 in tension with the assistance of lead spacers 34, which separate adjacent sheets 20 at the sheet ends, and are held in position by rods 24 passing through holes in the spacers. Each sheet 20 is 0.15 mm thick, 30 mm wide, and 80 mm long. Lead spacers 34 are 0.85 mm by 15 mm by 30 mm plates. Spacers 34 and rods 24 together form the two other sides of frame 18 in addition to sides 22.

Sheets 20 are equidistantly spaced 0.85 mm from each other to define fifty slits 36, which are 50 mm by 30 mm by 0.85 mm. The previously described tensioning of sheets 22 maintains these slit dimensions.

Figure 4:
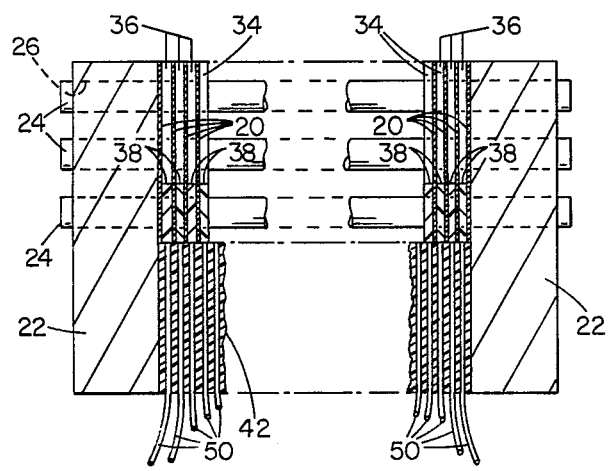
FIG. 4 is a view through 4—4 of FIG. 3, with portions broken away.
Figure 5:
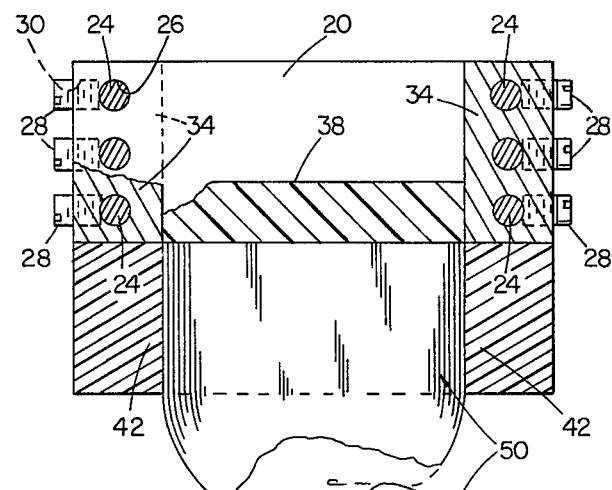
FIG. 5 is a view through 5—5 of FIG. 3, with portions broken away.

Detector 14 comprises fifty detector elements 38, which are scintillating sheets made of commercially available scintillating plastic composed mainly of polyvinyl toluene and manufactured and sold by Nuclear Enterprises, San Carlos, California. Each sheet 38 is 50 mm by 10 mm by 0.85 mm, and is fitted between each pair of adjacent tungsten sheets 20. With frame 18 directed toward a radiation source so that slits 36 are most favorably positioned to receive radiation from the source, each slit has an opening closest to the source to receive radiation and a base at the opposite end of the slit and the edges of sheets 38 that are farthest from the radiation source are positioned flush with the edges of the tungsten sheets 20 that likewise are farthest from the radiation source (FIGS. 4 and 5).

Figure 7:
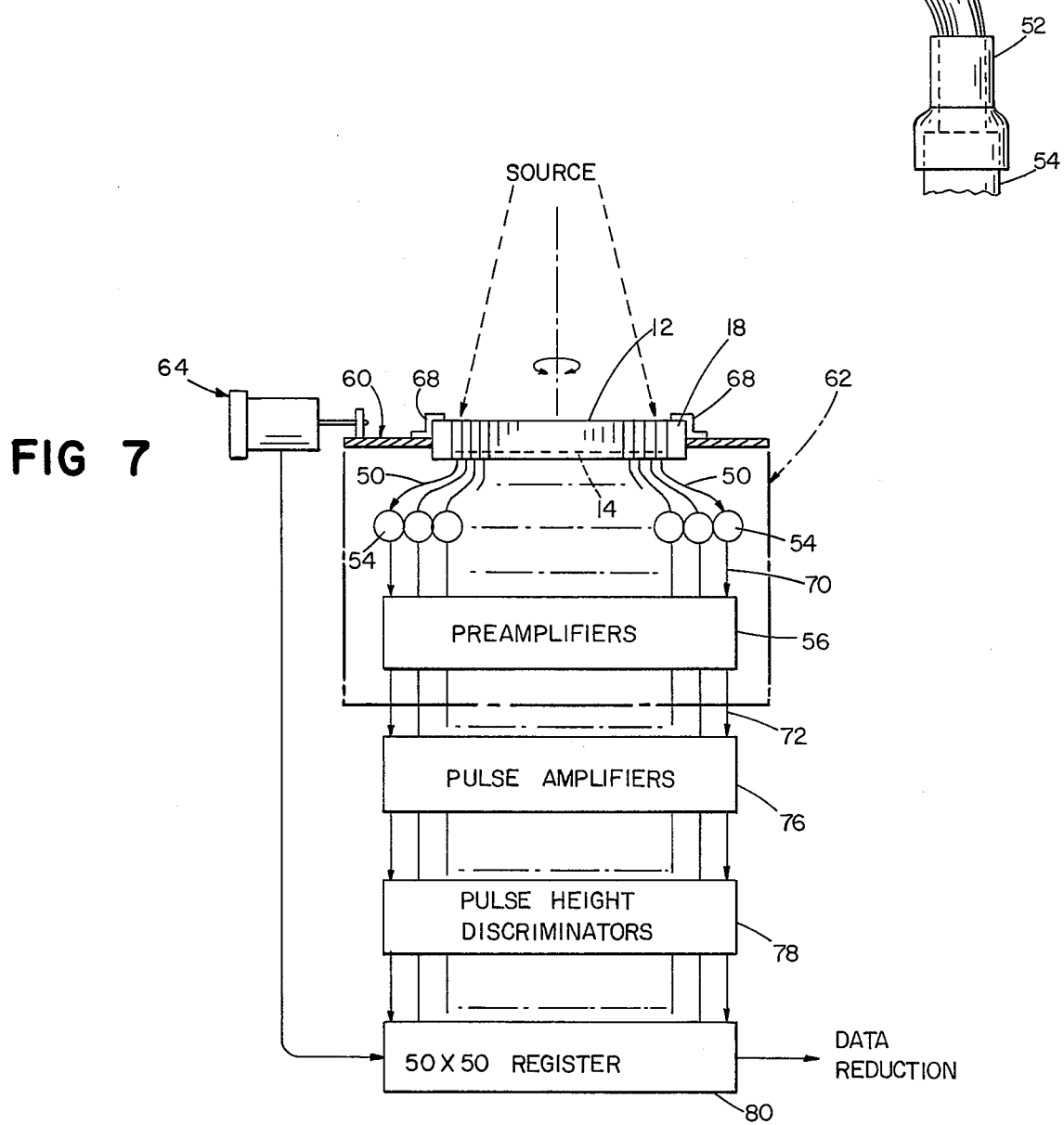
FIG. 7 is a diagrammatic view of the embodiment of FIGS. 2 through 6, with associated circuitry.

Attached by transparent epoxy to the rear face of each scintillating sheet 38 is a ribbon 50 of optical fibers (diagrammatically shown in FIGS. 4 and 5) having the same dimensions in cross-sectional area as does the rear face of sheet 38 (50 mm by 0.85 mm). Each ribbon 50 is composed of approximately 8 layers of 0.1 mm diameter fibers, about 500 fibers per layer, all produced by conventional fiber optic techniques. The fibers extend perpendicularly away from the rear face of sheet 38. All fifty ribbons 50, one for each sheet 38, are potted together in transparent epoxy, forming block 42, which extends 25 mm outwardly from the rear faces of sheets 38. Frame sides 22 likewise extend 25 mm below the rear faces of sheet 38, to provide a frame for the block of potted fibers. Conventional clamps (not shown) can be used to assist frame sides 22 in gripping block 42, which extends the length of sides 22. As they extend out of block 42, the fibers making up each ribbon 50 are independently flexible, and are gradually drawn together into a circular bundle, maintained in that position by ferrule 52. The ends of each circular fiber bundle are bonded to the sensor face of photomultiplier 54, which converts light signals to electrical ones for transmission to preamplifier 56 (FIG. 7). The optical fiber connection between detector array 14 and each photomultiplier 54 is flexible enough to accept a 180° rotation of plate 60.

Collimator 12, detector 14, fiber ribbons 50, photomultipliers 54, and preamplifiers 56 are all mounted in housing 16. Housing 16 includes circular steel mounting plate 60, steel tube 62, plate drive 64, and support arms 66. Frame 18 fits within a square hole centrally placed in mounting plate 60, clamps 68 holding frame 18 in place in plate 60. Plate 60 is fitted within the forward opening of tube 62, and is rotatable with respect to tube 62, a conventional bearing arrangement (not shown) permitting the rotation. Plate drive 64, including a reversible, indexed electric motor and timer, rotates plate 60, whose outer rim is toothed to provide a gear linkage (not shown) with drive 64. Frame 18, collimator 12, and detector array 14 all rotate with plate 60, which is driven discontinuously by drive 64.

Tube 62 is itself pivotally mounted on support arms 66 so that the tube can be tilted toward a particular radioactive source. Locking knob 44 is adjusted to hold tube 62 in the position chosen. Support arms 66 are mounted on a base (not shown), which conveniently includes casters, so that camera 10 as a whole can be wheeled to different positions.

FIG. 7 shows in block diagram conventional circuitry for processing electrical signals from photomultipliers 54. Signals from photomultipliers 54 are in the form of electrical pulses, each pulse corresponding to the absorption of a gamma ray by the corresponding scintillating sheet 38. These electrical pulses are transmitted to preamplifiers 56 through fifty leads 70 from the fifty photomultipliers 54. Preamplifiers 56 are located in the rear portion of tube 62, just forward of a steel circular backplate (not shown) covering the rear opening of tube 62. A hole through the center of the tube backplate permits fifty leads 72 channeled through flexible conduit 74 to pass from preamplifiers 56 out of tube 62. Preamplifiers 56 amplify all pulses coming from photomultipliers 54, and are placed in tube 62 to shield them from noise. The rest of the circuitry of FIG. 7 is conveniently housed in the mobile base. The amplified pulses travel through leads 72 to 50 pulse amplifiers 76, one for each lead, where the pulses are further amplified. The pulses are then transmitted from the 50 pulse amplifiers 76 to 50 pulse-height discriminators 78, which reject pulses having less than a predetermined amplitude (such as pulses caused by Compton effect photons), and permit the rest of the pulses to pass. Finally, the pulses are counted, and their number entered, in register 80. Register 80 is a 50 × 50 register, and is synchronously connected to plate drive 64, so as to count the pulses coming from the fifty pulse-height discriminators for each discrete angular position of collimator 12 and detector 14. This data made up of pulse counts is stored in register 80, and, when all counts have been made, is subsequently reduced by known computer techniques, to be explained in more detail below, to a form which identifies the two-dimensional location of the radiation sources impinging on collimator 12 and detector 14.

In operation, camera 10 is positioned so that the front of collimator 12 is as close to the radiation source as possible. The source itself is composed of Technetium 99, a radioisotope that emits gamma radiation with a characteristic energy of 140 Kev, or of some other radioisotope suited to clinical or other useful service. If the source is within a patient, collimator 12 is preferably brought into contact with the patient in the vicinity of the source. The source itself, for purposes of data analysis, may be regarded as a three-dimensional array of point sources randomly emitting gamma photons. Camera 10 in effect takes a picture of the two-dimensional array resulting from the orthogonal projection of this three-dimensional source array upon detector 14.

Collimator sheets 20 and collimator slits 36 are initially vertically aligned, and the axis of tube 62 is then aimed directly at the source volume (usually at the part of the patient's body to which the isotope has traveled). Locking knob 44 maintains the tube orientation. Photomultipliers 54 are activated, ready to respond to light signals from detector 14, and the signal processing equipment of FIG. 7 is energized. Collimator 12 remains in the vertical position for the order of 10 seconds, during which time gamma photons travel from the source to collimator 12, and enter the most favorably positioned slits 36. Plate drive 64 then rotates collimator 12 through 3.6°, followed by a ten-second pause, followed by another 3.6° step, and so on until fifty such steps of 3.6°, amounting to 180°, have been taken. The number of rotational steps for each 180° turn (here, fifty) is chosen to equal the number of slits 36 in collimator 12. During each ten-second interval, tungsten sheets 20 absorb any photons hitting the sheets. Photons passing from a particular point source through a particular slit solid angle subtended by the area of the incident face of a scintillating sheet 38 will pass into that scintillating sheet, and most will be absorbed therein, thereby exciting visible photons in the sheet. These visible photons are transmitted through sheet 38, and illuminate optical fibers in the ribbon 50 attached to the particular scintillating sheet. All faces of scintillating sheet 38 except the face bonded to ribbon 50 are coated with a substance reflective of visible light so that all visible light pulses excited within sheet 38 are eventually transmitted toward the rear face of sheet 38 and ribbon 50, though with higher attenuation of pulses undergoing one or more reflections before reaching ribbon 50. Attenuation of the visible light signals also occurs within ribbon 50, and about 1% of the visible light photons generated in sheets 38 reaches photomultipliers 54. However, the signals reaching the photomultipliers are sufficient to provide a basis for accurately determining the location of the sources of radiation.

Scintillating sheet 38 gives an output indicative of the energy of the incident gamma photon; thus photons of energy lower than the primary gamma photons arising from Compton scattering and originating at sites remote from the primary radiation sources can be rejected in pulse-height discriminator 78. During the ten-second interval before collimator 12 takes its first 3.6° step, and during each of the forty-nine subsequent 10-second intervals between subsequent 3.6° steps, each scintillating sheet 38 is collecting gamma photons from all radioactive point sources lying in the lamina of space created by projecting the pair of tungsten sheets 20 bounding sheet 38 toward the sources. Likewise during that interval each sheet 38 is collecting all the radiation emitted by each point source within the solid angle subtended by the area of the frontal face of sheet 38 with respect to that point source. The output of each scintillating sheet 38 at each rotational position is thus a series of visible light pulses corresponding to a series of gamma photon absorptions within the sheet, the photons coming from the various point sources.

the procedure for processing the data stored in register 80 to construct an image of the radioisotope source distribution is grounded preliminarily on the assumption that the distribution to be imaged will appear the plane perpendicular to the first direction as a two-dimensional array of 50 × 50 source elements. The problem then becomes that of constructing an image with 50 × 50 resolution elements, i.e., solving for 50 × 50 = 2500 unknowns. The isotope will be located wherever the value of the source element is nonzero, and will be absent where the value of the source element is zero. In principle, when there are 50 × 50 unknowns, it is always possible to solve for those unknowns with a system of 50 × 50 simultaneously linear equations. The steps of setting up the equations in matrix form and solving by the procedures of matrix algebra constitute a well-known direct approach to finding the unknowns. Register 80 provides the data from which 50 (slits) × 50 (angles) = 2500 equations can be constructed. Computer-performed mathematical techniques are presently at a point where expedited solution of this number of simultaneous equations can be accomplished. The following reference, hereby incorporated by reference herein, set forth methods for such expedited solutions: Ramachandran and Lakshminarayanan, "Three Dimensional Reconstruction From Radiographs and Electron Micrographs: Applications of Convolutions Instead of Fourier Transforms," Proceedings of the National Academy of Sciences of the United States, 1968, pp. 2236-2240; Gordon and Herman, "Three Dimensional Reconstruction from Projections: A Review of Algorithms," International Review of Cytology, Vol. 38 (1974) DeRosier and Klug, "Reconstruction of Three Dimensional Structures from Electron Micrographs," 217 Nature 130 (1968); and M. M. Woolfson, An Introduction to X Ray Crystallography, Chapter 4, "Fourier Transforms" (Cambridge Univ. Press 1970).

It is clear that radiation emitted from the peripheral regions of the source area will enter the camera with a somewhat lower probability of being accepted by the detector array than will radiation emitted from regions close to the axis of rotation of the collimator. Therefore it will be necessary to "weight" the data processing procedure so as to compensate for this bias. In the quoted references it is shown how this compensation may be achieved.

Because the resultant image created by these computer techniques is a two-dimensional one, though the radiosotope itself actually occupies three-dimensional space, the further technique, well-known in the field of radiation therapy, of taking additional pictures from different spatial positions of the collimator and combining them to produce a three-dimensional image is used. In the case in which the radioisotope is in the brain, the simplest method of carrying out this technique would be to take one picture with the axis of the collimator directed between the patient's eyes and to take a second picture with the collimator axis shifted 90° so as to be directed through the patient's ears.

A comparison of camera 10 with a conventional static channel collimator-detector system shows that sensitivity is improved with camera 10 and thus exposure time reduced without any impairment of resolution.

Furthermore, integration of detector 14 with the collimator 12 improves the overall spatial resolution of the image in two respects. First, if the detector 14 and collimator 12 be considered as separately constructed devices without attempt at registration between individual slits 36 and detector element 38, as is normally the case with existing channel collimating structures, then the effective resolution of the complete system is generally considered to be the square root of the sum of the squares of the minimum resolution distances of the two devices (the collimator and the detector) taken separately. Therefore if the spatial resolutions of the two devices are similar, integration of the detector with the collimator will yield an overall resolution improvement by a factor of the square root of two. Second, and more important, integration of the detector 14 with collimator 12 will essentially eliminate the loss of resolution incurred through scattering of radiation either within the collimator or within the detector array itself.

FIGS. 8 through 10 show a second embodiment of the invention using the same collimator 12 but a different detector 46. Detector 46 is composed of fifty detector elements 88, which are strips of photoconductors 90, five of which are spaced by polyethylene terephthalate insulation spacers 91 to form each strip. Each cadmium telluride photoconductor 90 is a rectangular crystal wafer measuring 10 mm by 5 mm by 0.75 mm, and each strip 88 of wafers is thus approximately 50 mm long. Deposited on the two largest faces of each photoconductor 90 is a pair of electrodes 92. Each electrode 92 itself comprises a thin layer of platinum deposited directly on the cadmium telluride body, thereby forming an electrode-cadmium telluride-electrode sandwich. The deposited layers 92 are each on the order of a micron in thickness. Resting flush against one side of strip 88 and extending parallel to the strip is ground connector 98. Ground connector 98 is a strip of polyethylene terephthalate manufactured and sold by du Pont under the trademark Mylar on which a thin aluminum coating has been deposited. The thickness of this Mylar-aluminum strip is approximately fifty microns, with the Mylar accounting for most of the thickness. An aluminum-Mylar ground finger 100 extends downward from strip 98 toward one end thereof. The aluminum face of ground connector 98 is positioned on one side of strip 88. The Mylar gives strength to the aluminum connector while serving as an insulator between an adjacent tungsten sheet 20 and the aluminum connector. A similar connector 102 is positioned on the other side of strip 88, but the aluminum coating has been divided, by prior removal of narrow vertical bands of aluminum, into five electrically isolated regions 104 corresponding to the five photoconductors 90 making up strip 88. Each of the five aluminum regions 104 has an aluminum-Mylar finger 106 extending downward from the region. The whole connector-electrode-photoconductor-electrode-connector sandwich that results when all these elements are brought together is positioned between each pair of adjacent tungsten sheets 20 of collimator 12 as well as between one frame side 22 and an adjacent tungsten sheet 20. This sandwich structure measures 50 mm by 5 mm by 0.85 mm, and takes the place of scintillating sheet 38 in slit 36. A strip 88 of photoconductors 90 accounts for most of the thickness of the connector-electrode-photoconductor sandwich in each slit 36 so that only a small fraction of the indicent gamma photons in slit 36 will be lost by entering the connectors 98, 102 or the electrodes 92. Photoconductor strips 88 and conductors 98 and 102 are supported by printed circuit board 108. Board 108 is slotted at appropriate locations to receive ground fingers 100 and fingers 106. The fingers pass to the underside of board 108, where a printed ground lead (not shown) connects the ground fingers 100 for all the ground connectors of the detector array and where separate printed leads (not shown) are individually connected to each of fingers 106. Photoconductor strips 88 rest along their lower faces on board 108. Tungsten sheets 20 are also grounded by connection to the ground lead of board 108 (the connections are not shown). Strips 88, by virtue of Mylar spacers inserted at the strip ends, and the aluminum portions of connectors 98 and 102, by removal of bands of aluminum at the ends, are also insulated from lead spacers 34, which as before are fitted between sheets 20, and form two borders for the detector array. Board 108 is itself secured to frame sides 22 by brackets (not shown).

Voltage source 110 (50 volts) (FIG. 9) is connected through board 108 and connectors 98 and 102 so as to apply its voltage through each pair of electrodes 92 across each photoconductor 90 (there are 5 × 50 = 250 photoconductors 90). The output signal from each photoconductor 90 is carried out through connectors 98 and 102 to printed leads in board 108 and from there through flexible leads 112 to a preamplifier 56a. There are 250 preamplifiers in all, one for each photoconductor 90. The output signals from five preamplifiers 56a corresponding respectively to the five photoconductors 90 in a strip 88 are combined and fed into a pulse amplifier 76. As with the embodiment using detector array 14 and photomultipliers 54, there are fifty pulse amplifiers 76, 50 pulse-height discriminators 78, and one register 80. Each preamplifier 56a is an operational amplifier with a field effect transistor input, a open-loop gain of $10^5$, and an input current sensitivity of $10^{-11}$ ampere.

An incident gamma photon producing a charge of $10^{-14}$ coulombs in the photoconductor crystal, and with the entire charge collected at the pair of electrodes 92 in a micro-second, the current output is $(10-14/10^{-6}) = 10-8$ ampere, which can be recognized and amplified in preamplifier 56. Because the Mylar insulation on connectors 98 and 102 is kept thin so that the area of the radiation-exposed surface of photoconductor 90 can be maximized, a large capacitance (in relation to the capacitance across the photoconductor 90) is developed across the Mylar between each tungsten sheet 20 and the aluminum coating of connectors 98 and 102. This capacitance might ordinarily reduce the voltage excursion of any signal coming from electrodes 92 below limits detectable by preamplifier 56, but the segmenting of detector strip 88 into five separate photoconductors 90 results in an overall capacitance for each photoconductor 90 one-fifth as large as the total capacitance of strip 88, an acceptable value as far as retrieval of signals from photoconductor 90 is concerned. In regard to sensitivity, with a preamplifier 56a capable of detecting incoming signals down to $10^{-11}$ ampere, accurate measurement of the magnitude of expected signals on the order of $10^{-8}$ ampere is possible. Thus it is possible to screen out the lower energy Compton photons downstream in the pulse-height discriminators 78. The overall background noise is approximately equivalent to a 10 Kev signal so that discrimination between genuine source photons and noise is possible, using radiation sources of more than about 20 Kev.

the thin strip design of photoconductors 90, with electrodes 92 positioned parallel to the collimator sheets 20, though bringing with it a capacitance problem as just described, offers simultaneously the advantages of a short interelectrode distance and a long photon absorption distance. By having a relatively short distance between opposing electrodes 92 (about 0.75 mm), the current carrier (electron or hole) collection efficiency of the electrodes is improved, with resultant improvement in obtaining uniformity of response for photon excitations, and the carrier collection time is reduced, with resultant improvement in temporal resolution. By having a relatively deep photoconductor crystal (5 mm), most incoming photons from a 140 Kev or less isotope source will be absorbed by the crystal, providing better camera sensitivity. In general, with use of photoconductors signal losses are far lower than with scintillating sheets and optical fibers, and energy resolution is much improved. With more of the signal actuually reaching preamplifier 56a, more accurate imaging is the result.

Methods for processing the data received in register 80 are as previously described, and the improvement in sensitivity over the channel collimator is also as previously described.

Regarding modifications in procedure and structure, collimator 12 can be continuously rotated rather than discontinuously rotated, or even operated moving its axis along another curved or other configuration or without rotation. Symmetry about the axis is preferred but not essential. Appropriate modifications in the data reduction procedures will then be required, of course. If harder radiation sources than Technetium 99 are used, scintillating sheets 38 and photoconductors 90 will need to be deeper from top to bottom (i.e., have a longer photon absorption distance). If, for example, the source is on the order of Mev's, photoconductor 90 may need to be 40 to 50 mm deep rather than only 5 mm. If greater resolution is desired, the number of slits in collimator 12 can be increased accordingly, to at least a total of 250 slits; assembly of such a collimator would understandably be somewhat more involved than in the case of the fifty-slit collimator. Tantalum can be used in place of tungsten in sheets 20. Polystyrene can be used in place of polyvinyltoluene in scintillating sheets 38. Finally, in photoconductor detector 46, copper can be used instead of aluminum in connectors 98 and 102, electrodes 92 can be made thicker, for better uniformity of response (though possibly at the sacrifice of effective photoconductor area), electrodes 92 can include a thin layer of a conductor such as indium deposited on the platinum to improve contact between the platinum and the metallic coating of connectors 98 and 102, and photoconductor strips 88 can be continuous instead of segmented if the excited signals are strong enough to overcome the capacitance problem. Additionally, instead of photoconductor detector 46, a detector comprising a continuous planar sheet of photoconductor material having electrodes formed in strips and deposited on top and bottom instead of one of the sides, as in detector 46, could be employed. Construction is made easier, but such a detector does not have the combined advantage of both high photon collection efficiency and improved charge carrier collector efficiency of detector 46.

Other embodiments within the invention will be apparent to those skilled in the art.

While I have shown and described, for simplicity, a 50 mm by 50 mm device, my most preferred embodiment is a 250 mm by 250 mm device, each slit being the same width as in the embodiment shown and described, but five times as long, and there being 250 slits rather than 50. My most preferred detector is the semiconductor structure disclosed. Preferably after stepping through 180° my camera through a flyback returns to its initial position. In preferred embodiments slit length is at least ten times slit width; in my most preferred embodiments it is at least fifty times slit width.

While it might be thought, as it was by some to whom I initially disclosed my invention, that the increased flux available in each position with slits instead of holes would be an advantage neutralized by the increased number of positions required to be used, surprisingly this proved untrue, owing to improved signal to noise ratios, permitting increasing speed as well as resolution.

What is claimed is:

1. An instrument for obtainingg positional source information which comprises:

a slit collimator containing a multiplicity of slits for reception therein of beam components moving in a straight line from a source, each slit of said slits including an open end for orientation toward said source and slit-defining walls extending inwardly from said open end, said walls extending in the same longitudinal direction, said walls including material of character and thickness to absorb those of said beam components impinging thereon, and said slits extending further in one transverse direction than in the other transverse direction; and a detector for separately detecting beam components passing through said slits, said detector being fixedly mounted relative to said collimator.

2. The instrument of claim 1 which includes also a positioner, said positioner being interconnected with one of said collimator and said source so as to simultaneously change the transverse position of said slits relative to said source.

3. The instrument of claim 1 in which the ends of said slits opposite each said open end are closed by said detector.

4. The instrument of claim 1 in which each said slit extends at least ten times as far in said one transverse direction as in said other transverse direction.

5. The instrument of claim 3 in which each said slit extends fifty times as far in said one transverse direction as in said other transverse direction.

6. A device for obtaining information about the distribution of radiational and particle sources, said device comprising:

a collimator including a frame having an axis of rotation defining a first direction and a plurality of planar sheets of gamma-radiation-absorbing material maintained by said frame in parallel, spaced-apart relation with respect to each other and parallel with said axis of rotation, adjacent pairs of said sheets defining slits therebetween, each of said slits having an opening at one end thereof and a base at the opposite end thereof, and being unimpeded, within said frame, in a second direction perpendicular to said axis of rotation and parallel with said sheets, means for positioning said collimator to maintain said axis of rotation pointed at a gamma radiation source so that said slits are disposed to receive gamma radiation therefrom while said collimator is rotated about said axis, each of said slits subtending, in the plane defined by said first and second directions, a much larger angle for receiving said radiation passing therethrough to said base thereof from said source than it subtends in a second plane perpendicular to said second direction, a detector effectively connected to said frame for common rotation with said collimator and positioned adjacent the bases of said slits for detecting radiation passing through each slit to the base thereof and providing an output representative of the intensity of detected radiation over the whole of said base as a function of the angle of rotation of said collimator, and means for accumulating a matrix of said outputs, said matrix being ordered according to the particular slit in which the radiation causing said output was detected and according to the particular angle of rotation of said collimator at the time said radiation was detected, said matrix being suitable for transformation to a matrix corresponding to the image of said source.

7. The device of claim 6 wherein said detector comprises a plurality of detector elements equal in number to said slits, each of said detector elements being positioned adjacent said base of each of said slits for detecting radiation passing through each slit to the base thereof and providing said output, said detector elements being effectively connected to said frame so that they remain positioned adjacent their respective bases while said collimator is rotated about said axis.

8. The device of claim 6 further comprising processing circuitry including an amplifier for amplifying said outputs, and an amplitude discriminator for transmitting components having a minimum amplitude and discarding the rest;

whereby components resulting from radiation below a predetermined energy threshold are discarded.

9. The device of claim 8 wherein said means for accumulating comprises a register for accumulating the outputs amplified by said amplifier and transmitted by said discriminator.

10. The device of claim 6 wherein said maintaining means comprises a housing for said collimator, said housing including a tube, a plate rotatably mounted in said tube, and means for rotating said plate, said plate containing an aperture for receiving said frame so that when said plate is rotated, said frame is rotated together therewith.

11. the device of claim 10 wherein said rotating means is an indexed motor adapted to rotate said plate in discrete angular steps.

12. The device of claim 6 wherein said sheets of said collimator are made of tungsten foil.

13. The device of claim 7 wherein said collimator has from fifty to two hundred and 50 slits and said detector has an equal number of detector elements.

14. The device of claim 7 wherein each said detector element includes a scintillating sheet and a photomultiplier connected to said sheet for providing an electrical output.

15. The device of claim 14 wherein said scintillating sheet is connected to said photomultiplier by a plurality of optical fibers.

16. The device of claim 13 wherein said collimator has fifty slits and said detector has 50 detector elements.

17. The device of claim 7 wherein said detector elements are positioned between the sheets of said collimator at the base of said slits.

18. The device of claim 7 wherein said detector element is a photoconductor element.

19. The device of claim 17 wherein said detector element is a photoconductor element.

20. The device of claim 18 wherein said photoconductor element is composed of cadmium telluride.

21. The device of claim 18 wherein said photoconductor element includes a pair of electrodes the plane, of which are parallel to the sheets of said collimator and the distance through said photoconductor in said first direction is large with respect to the distance between said pair of electrodes in a third direction perpendicular to said first and second directions.

22. The device of claim 21 wherein said distance in said first direction is no less than 5 mm and said distance in said third direction is no greater than 0.75 mm.

23. The device of claim 6 wherein said frame is rectangular and composed of two opposite side pieces joined by a rod at each end thereof, said collimator sheets having holes at their ends for receiving a said rod through each end thereof.

24. A method of obtaining information about the distribution of a gamma radiation source, said method comprising the steps of:
providing a collimator including a frame having an axis of rotation and a plurality of planar sheets of gamma radiation absorbing material maintained by said frame in parallel, spaced-apart relation with respect to each other and parallel with said axis of rotation,
adjacent pairs of said sheets defining slits therebetween, each of said slits having an opening at one end thereof and a base at the opposite end thereof and being unimpeded, for permitting passage of gamma radiation therethrough, in a first direction parallel to said axis of rotation and being unimpeded, within said frame, in a second direction perpendicular to said axis of rotation and parallel with said sheets,
positioning said collimator to maintain said axis of rotation pointed at a gamma radiation source so that said slits are disposed to receive gamma radiation therefrom while said collimator is rotated about said axis, each of said slits subtending, in the plane defined by said first and second directions, a much larger angle for receiving said radiation passing therethrough to said base thereof from said source than it subtends in a second plane perpendicular to said second direction,
rotating said collimator about said axis while maintaining said axis pointed at said source,
detecting distinctly radiation passing through each slit to the base thereof and deriving an output representative of the intensity of radiation detected over the whole base of each slit as a function of the angle of rotation of said collimator,
accumulating a matrix of said signals, said matrix being ordered according to the particular slit in which the radiation causing said output was detected and according to the particular angle of rotation of said collimator at the time said ratiation was detected, and
transforming said matrix to a matrix that corresponds to the image of said source.

25. The method of claim 24 wherein said rotating is done discontinuously in a series of angular steps equal to the number of slits in said collimator.

26. The method of claim 24 wherein said transforming step comprises inverting said matrix of outputs.

27. A detector for detecting gamma radiation and for providing an output in response to said radiation, said detector comprising:
a plurality of detector elements of photoconductor material sensitive to gamma radiation,
said elements being strips arranged in parallel, spaced-apart relation, to expose to incident gamma raditaion, from a source of the same, a generally planar surface made up of one face from each of said elements,
each of said elements having a pair of electrodes affixed thereto, each one of said pair of electrodes being positioned between adjacent elements, the planes of said electrodes being perpendicular to said planar surface exposed to incident radiation, and
the thickness of each said detector element measured from said surface exposed to incident radiation along a perpendicular line therefrom is large with respect to the distance between each said pair of electrodes, wherein said thickness measured from said surface exposed to incident radiation is at least 5 mm and said distance between each said pair of electrodes is no greater than 0.75 mm.

28. A detector for detecting gamma radiation and for providing an output in response to said radiation, said detector comprising:
a plurality of detector elements of photoconductor material sensitive to gamma radiation,
said elements being strips arrannged in parallel, spaced-apart relation, to expose to incident gamma radiation, from a source of the same, a generally planar surface made up of one face from each of said elements,
each of said elements having a pair of electrodes affixed thereto, each one of said pair of electrodes being positioned between adjacent elements, the planes of said electrodes being perpendicular to said planar surface exposed to incident radiation, and
the thickness of each said detector element measured from said surface exposed to incident radiation along a perpendicular line therefrom is large with respect to the distance between each said pair of electrodes, wherein each of said strips is made up of a plurality of detector crystals bonded together but electrically insulated with respect to each other.

29. The method of obtaining positional source information which comprises
collimating beam components moving in a straight line from said source in a multiplicity of slits parallel in a beam-recieving longitudinal direction having one transverse dimension at least ten times the other transverse dimension, and having beam-component absorptive walls,
separately detecting beam components entering open ends of said slits and traversing said slits without absorption,
changing the relative transverse position of said slits and said source and repeating said collimating and detecting steps,
repeating the last-mentioned step a multiplicity of times, and
processing the detection data to acquire said information.

* * * * *